(12) United States Patent
Stamatoukos (10) Patent No.: US 9,016,136 B1
(45) Date of Patent: Apr. 28, 2015

(54) APPARATUS FOR TESTING ADHESION OF AN ADHESIVE TAPE TO A BONDING SURFACE UNDER A LOAD APPLIED TO THE TAPE

(71) Applicant: Shurtape Technologies, LLC, Hickory, NC (US)

(72) Inventor: George Stamatoukos, Hickory, NC (US)

(73) Assignee: Shurtape Technologies, LLC, Hickory, NC (US)

( * ) Notice: Subject to any disclaimer, the term of this patent is extended or adjusted under 35 U.S.C. 154(b) by 108 days.

(21) Appl. No.: 13/795,909

(22) Filed: Mar. 12, 2013

(51) Int. Cl.
*G01N 3/24* (2006.01)
*G01N 19/04* (2006.01)

(52) U.S. Cl.
CPC ...................................... *G01N 19/04* (2013.01)

(58) Field of Classification Search
CPC .......... G01N 19/04; G01N 2203/0044; G01N 2203/0091; G01N 2203/0025
USPC ........... 73/827, 831, 842, 856, 150 A; 209/45
See application file for complete search history.

(56) References Cited

U.S. PATENT DOCUMENTS

| | | | |
|---|---|---|---|
| 3,019,644 A * | 2/1962 | Mancini | 73/150 A |
| 3,396,578 A * | 8/1968 | Skundberg | 73/150 A |
| 4,888,985 A * | 12/1989 | Siemer | 73/150 A |
| 2012/0103081 A1 * | 5/2012 | Hoshino | 73/150 A |
| 2012/0123700 A1 * | 5/2012 | Tsaur | 702/41 |

OTHER PUBLICATIONS

Author: unknown, Title: TH2450 motorised transporabel peel jig, URL: http://www.grip.de/G14, date: waybackmachine date of Jan. 30, 2011, Publisher: Grip-Engineering, Thuemler GmbH, pp. 3.*
Walnut Industries Inc., brochure title "TY-Gard 2000, Cargo Restraint System", Copyright 2009, pp. 1-8, published by Walnut Industries Inc. on company's website address: http://ty-guard2000.com/products.html.
Walnut Industries Inc., brochure title "TY-Tool", Copyright 2009, pp. 1-2, published by Walnut Industries Inc. on company's website address: http://ty-guard2000.com/products.html.

* cited by examiner

*Primary Examiner* — Harshad R Patel
(74) *Attorney, Agent, or Firm* — Nelson Mullins Riley & Scarborough LLP (57) ABSTRACT

Apparatus for testing adhesion of an adhesive tape to a bonding surface under an applied load includes a test surface of a predetermined configuration to which a test tape may be adhered, a clamping device for grasping a free edge of the test tape, a guide for constraining the clamping device to move linearly relative to the test surface, and an actuator arrangement for driving the clamping device along the guide at a selected speed and with a selected force to apply the force to the test tape. The actuator arrangement includes a first and second linear actuators operable to generate differing ranges of force values, a motor for driving the linear actuators, and a selector arrangement for connecting the motor alternately to the first and second linear actuators according to the selected force to be applied.

28 Claims, 9 Drawing Sheets

APPARATUS FOR TESTING ADHESION OF AN ADHESIVE TAPE TO A BONDING SURFACE UNDER A LOAD APPLIED TO THE TAPE

FIELD OF THE INVENTION

The present invention relates to adhesive tapes and, more particularly, to the testing of the adhesion qualities of a tape under load, e.g., against shear and/or peel forces.

BACKGROUND OF THE INVENTION

Adhesive-backed pressure-sensitive tapes vary considerably in many respects, e.g., as to size, substrate or tape body material and construction, adhesive composition, and end-use applications, but apart from such diverse differences, it is recognized that substantially all adhesive tapes may be quantitatively and qualitatively evaluated according to their adhesion characteristics, particularly resistance to shear and peel forces, as a comparative measure of suitability for a designated end-use. Nevertheless, for many adhesive tapes, no accepted methodology or apparatus exists for systematically testing the adhesion qualities of the tape in a reliable and repeatable manner.

As one representative example, adhesive tape has begun to be commonly used to secure and restrain cargo during transport in shipping containers to prevent shifting movement and attendant damage to the cargo, the container, and/or the ambient environment. An example of such a cargo restraint system is the "TY-GARD 2000"® system produced by Walnut Industries, Inc., of Bensalem, Pa., which is particularly designed and intended for use in standard shipping containers as are commonly used for ocean, rail and truck transportation of cargo. Basically, the "TY-GARD 2000" system utilizes an elongate adhesive tape formed in a relatively large width (e.g., about 16 inches) of a plastic substrate including lengthwise-extending glass fibers backed with an adhesive composition, whereby two lengths of the tape may be secured adhesively to opposite interior side walls of a shipping container and then free ends of the two tape lengths secured together across the widthwise extent of the container, e.g., via a connecting "patch" of an additional length of tape overlapping the two free tape ends, to surround and secure a unit of cargo, e.g., a shipping pallet, against movement during shipment.

As will be recognized, the effectiveness of such a cargo restraint system is directly dependent upon the strength of adhesion of the tape to the sidewalls of the container and, since cargo can vary from drums of hazardous chemicals to complex electronic equipment to delicate breakables, it is critical that the adhesion qualities of the tape be reliably testable and measurable. Heretofore, however, the testing of such cargo restraint tapes has been extremely crude and primitive, e.g., by merely adhering a length of tape to a vertical surface, attaching a designated weight to a free end of the tape, and dropping the weight under the force of gravity to exert an impact stress upon the tape. As is apparent, while such a test may be of some indication of the reliability and effectiveness of a tape, the test lacks suitable controls for the test parameters to be precisely repeatable from one test to another and the results of tests cannot be quantitatively measured and compared. Accordingly, a significant need exists for testing apparatus and methodology by which test parameters can be precisely controlled and repeated and test results can be precisely measured.

SUMMARY OF THE INVENTION

The present invention seeks to provide an apparatus for testing adhesion of an adhesive tape to a bonding surface under a load applied to the tape, which overcomes the deficiencies of known testing methods.

Briefly summarized, the present apparatus comprises a test surface of a predetermined configuration to which may be adhered a length of adhesive tape to be tested, a clamping device for grasping a free edge of the adhesive tape to be tested, a guide for constraining the clamping device to move in a defined linear direction relative to the test surface, and an actuator arrangement for driving the clamping device along the guide at a selected speed and with a selected force to apply the force to the tape adhered to the test surface. More specifically, the actuator arrangement includes a first linear actuator arrangement operable to generate the selected force within a first range of force values, a second linear actuator arrangement operable to generate the selected force within a second range of force values, a motor for driving the linear actuators, and a first selector arrangement for selectively connecting the motor alternately to the first and second actuator arrangements according to the selected force to be applied to the clamping device.

As persons skilled in the relevant art will recognize, various and diverse embodiments and applications of the apparatus of the present invention are possible, all of which are deemed and intended to be within the scope of the present invention. For example, the motor may comprise an air compressor with an associated accumulator communicated with the air compressor to receive and store pressurized air. Each linear actuator arrangement may comprise a linear actuator and an associated plurality of valves, with each valve being operable for passage of pressurized air therethrough at a respective predetermined rate different from each other valve. The selector arrangement is operable for selectively communicating the selected active linear actuator with any selected one of the valves associated therewith to achieve a different associated force output from the linear actuator.

In a contemplated embodiment, the actuator arrangement may include a tether attached to the clamping device and selectively attachable alternately to the first and second linear actuators. More specifically, the tether may be of a selected length between the clamping device and a starting position of each of the linear actuators to be initially slackened upon actuation of the selected actuator for acceleration thereof to a selected speed before tautening of the tether to apply the selected force on the tested tape as an initial impact force and thereafter to maintain application of the selected force continuously on the tape.

The present apparatus may also comprise a sensor arrangement for detecting release of the tape from the test surface under the force applied by the actuator arrangement, as an indication of failure of the tape. For example, the sensor arrangement may comprise a plurality of photosensors directed at spacings along the test surface, to enable detection of progressive failures of the tape.

The apparatus may further comprise a frame to which the test surface, the clamping device, the guide, and the actuator arrangement are commonly mounted. More specifically, the frame, the test surface, the clamping device, the guide, and the actuator arrangement may be assembled as a unit, e.g., with the frame in the form of a wheeled cart, for portability of the apparatus for testing under differing selected ambient conditions. The apparatus may further comprise a control arrangement for remote actuation of the actuator arrangement, which may be advantageous for testing a tape under extreme or hazardous ambient conditions.

It is further contemplated that the test surface may be selectively attachable and detachable for interchange of multiple alternative test surfaces. The apparatus may further comprises a table surface to which the test surface is mounted and an adjusting arrangement for selectively setting the table in a horizontal disposition or a disposition inclined relative to horizontal, for selectively varying the direction of application of the selected force on the tape to be tested.

DETAILED DESCRIPTION OF THE PREFERRED EMBODIMENTS

Figure 1:
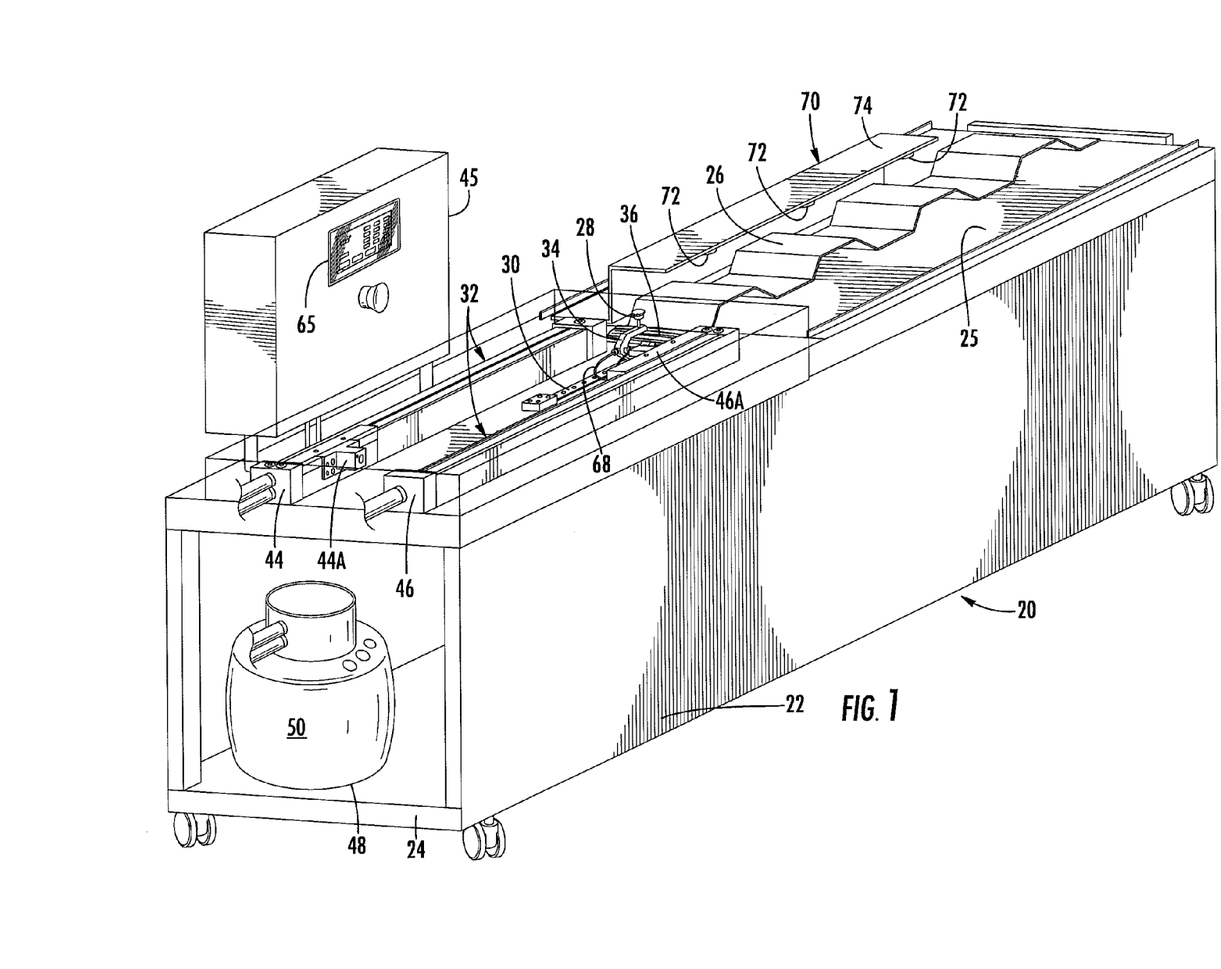
FIG. 1 is an overall perspective view of the testing apparatus of the present invention.
Figure 2:
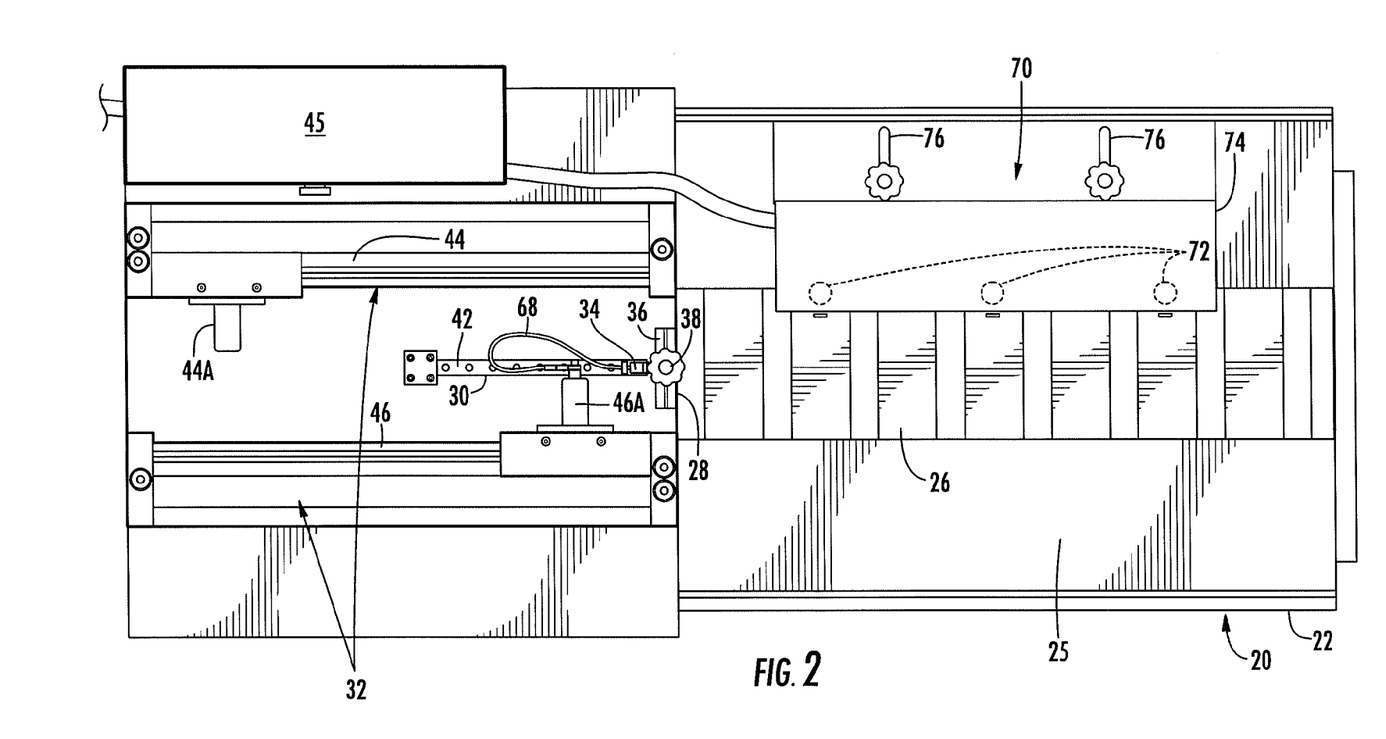
FIG. 2 is a top plan view of the testing apparatus of FIG. 1.

Referring now to the accompanying drawings and initially to FIGS. 1 and 2, an apparatus for testing adhesion of an adhesive tape is depicted overall at 20 according to a representative contemplated embodiment of the present invention. It is, however, expressly intended and to be understood that the illustration and description herein of such embodiment of the present invention is merely illustrative for purposes of providing an enabling disclosure of the invention for the understanding of those persons skilled in the relevant art, but is without limitation or restriction of the scope and applicability of the invention in other embodiments and other applications not inconsistent with the disclosure and claims herein.

The testing apparatus 20 basically comprises a frame 22, such as in the form of a wheeled cart 24, having a table surface 25 on which are mounted a test surface 26 to which a length of adhesive tape to be tested may be adhered, a clamping device 28 adapted for grasping a free edge of the adhesive tape to be tested, a guide 30 constraining the clamping device 28 to move in a defined linear direction relative to the test surface 26, and an actuator arrangement, indicated generally at 32, for driving the clamping device 28 along the guide 30 at a selected speed and with a selected force to apply the force to the tape adhered to the test surface 26, all as more fully explained below.

The test surface 26 is formed of a material, configuration and finish identical to or at least closely simulative of a surface to which the tape to be tested will ordinarily be applied in typical usage. As the apparatus 20 may be used for testing of various and differing tapes and any given tape may be adapted to use on various surfaces, the test surface 26 is removably affixed to the table surface 25 to facilitate interchange of one test surface for another when necessary or desirable. In the illustrated embodiment, the test surface 26 is in the form of a corrugated metal plate corresponding to the corrugated walls in cargo shipping containers to facilitate the testing of a cargo restraint tape such as the "TY-GARD 2000"® tape described above, but it is to be expressly understood that other test surfaces of other materials and configurations are equally contemplated to facilitate testing of other tapes.

The clamping device 28 may be of any suitable construction and configuration capable of grasping and maintaining a grasp on an edge of a tape under an impact and force loading as are imposed by the present invention. In the illustrated embodiment, the clamping device 28 comprises a rigid upwardly curving arm 34 to which is affixed a pair of gripping jaws 36 openable and closable mechanically relative to one another via a drive screw 38. The guide 30 may be of any suitable construction interactive with the clamping device 28 to define a linear path of reciprocating travel by the clamping device 28 toward and away from the test surface 26. In the illustrated embodiment, the guide 30 is a linear rail 42 mounted to the table surface 25 in linear alignment with the longitudinal extent of the test surface 26. A base portion of the arm 34 rests upon the rail 42 and is formed with a guide channel (not shown) through which the rail 42 extends.

The actuator arrangement 32 comprises two independent linear actuators 44, 46 affixed to the table surface 25 at opposite sides of and extending parallel to the guide rail 42, and powered by a suitable motor, indicated generally at 48, via a control system contained in a control housing 45, as more fully described below. Each linear actuator 44, 46 may be of a piston-and-cylinder construction adapted for dual-acting pneumatic operation, the actuator 44 having a lesser volumetric capacity and the actuator 46 having a greater volumetric capacity to accommodate the selected application of a range of forces via the clamping device 28 to a tape to be tested, also more fully explained below.

Figure 3:
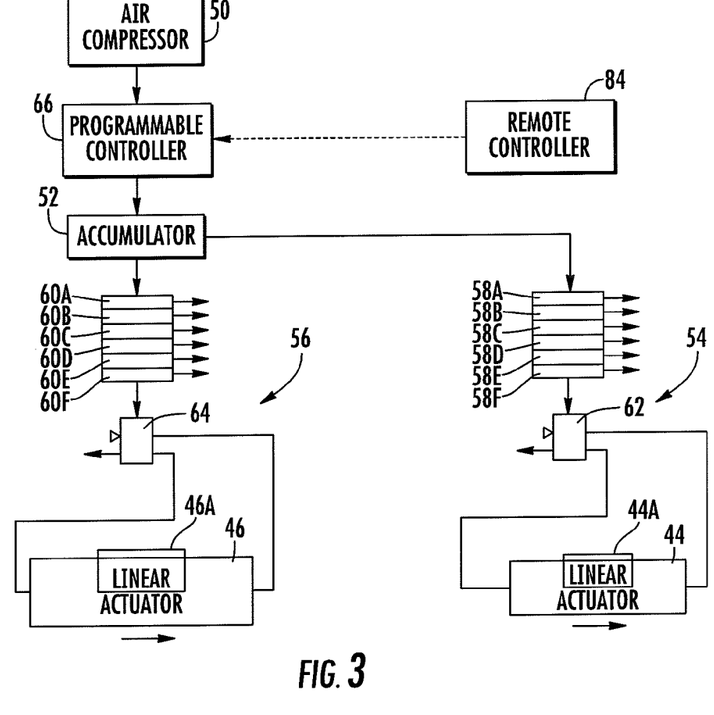
FIG. 3 is a schematic diagram depicting the pneumatic controls and operation for the testing apparatus of FIGS. 1 and 2.

Referring now to FIG. 3, the pneumatic actuating system for the actuator arrangement 32 is shown in a schematic airflow diagram. The motor 48 may be an electrically-powered air compressor 50 which continuously charges an accumulator 52 with pressurized air. The accumulator 52 communicates through an airflow circuit 54 with the linear actuator 44 and through an airflow circuit 56 with the linear actuator 46 to continuously pressurize each circuit 54, 56 and each actuator 44, 46. A plurality of solenoid exhaust valves 58A-58F in association with a multi-port solenoid actuating valve 62 are disposed in parallel to one another in the airflow circuit 54 and a similar parallel series of solenoid exhaust valves 60A-60F with an associated multi-port solenoid actuating valve 64 are disposed in the airflow circuit 56.

The exhaust valves 58A-58F and 60A-60F are of progressively differing port sizes to operate the associated linear actuators 44 or 46 at correspondingly different pneumatic pressures and thereby generate correspondingly different drive forces on the clamping device 28 and, in turn, on the tape to be tested. For example, in a contemplated embodiment, the exhaust valves 58A-58F may be differently sized to generate pneumatic pressures in the linear actuator 44 in 5 lb. (pound force) increments, e.g., 25 lbs., 30 lbs., 35 lbs., 40 lbs., 45 lbs. and 50 lbs., while the exhaust valves 60A-60F may be similarly sized differently to generate incrementally increasing pneumatic pressures in the linear actuator 46, e.g., 55 lbs., 60 lbs., 65 lbs., 70 lbs., 75 lbs. and 80 lbs. A selector arrangement, e.g., a programmable controller, indicated only schematically at 66, provides an arrangement for selectively actuating one exhaust valve 58A-58F or 60A-60F and its associated actuating valve 62 or 64 according to a desired force to be applied to the clamping device 28 and the tape to be tested. A control panel 65 associated with the programmable controller 66 is mounted on the control housing 45 for operator input of selected control settings, such as a selected force value (e.g., via a "Force lbs." input button), to initiate a test sequence, and also to display operational results of each test sequence, as more fully explained below.

Each linear actuator 44 and 46 includes an external drive bracket 44A, 46A, respectively, which may be attached to the arm 34 of the clamping device 28 via a tether 68, e.g., in the form of a cable. Upon actuation of a selected linear actuator 44 or 46, the actuating valve 62 or 64 in the associated airflow circuit 54 or 56 delivers pressurized air into the actuator to move the respective drive bracket 44A or 46A to the end of the actuator 44 or 46 most closely proximal the test surface 26, at which the drive bracket 44A or 46A is disposed to be manually connected to the clamping device 28 by the tether 68.

For certain tapes used in certain applications, it may be appropriate or desirable that a test sequence simulate an abrupt impact force imposed on the tape. For example, a cargo restraint tape of the type above-described will often be subjected to such impact forces in ordinary use, such as may occur upon acceleration or braking of a transport vehicle (e.g., a railroad car or a transport truck) or similar events (e.g., coupling of railroad cars together). In order to simulate the application of this type of force under testing conditions with the present apparatus 20, the tether 68 may be formed of a selected length such that, when connected between the arm 34 of the clamping device 28 and the drive bracket 44A or 46A of the selected actuator 44 or 46, the tether does not extend tautly but instead has an intentional amount of slack (as can be seen in FIGS. 1 and 2). Thus, upon driving actuation of the selected actuator 44 or 46, the actuator is accelerated to a predetermined speed before tautening of the tether 68 so as to apply a selected force on the tape to be tested as an initial impact force and thereafter to maintain application of the selected force continuously on the tape, again as will be more fully described below. However, it is also contemplated that testing of other tapes may be appropriate without imposing an initial abrupt impact force on the tape, in which case a rigid connection or a tethered connection without slack may be appropriate between the clamping device 28 and the drive bracket 44A or 46A of the selected actuator 44 or 46.

It is considered to be desirable that, in any testing of a given tape, the applied force setting (lbs.) be selected to induce a failure in the adhesion of the tape to the test surface 26, e.g., sufficient to pull the tape from the test surface 26. In turn, it is considered desirable that the present test apparatus include a sensor arrangement for detecting and recording the release of a tested tape from the test surface 26. For example, as indicated generally at 70 in the embodiment depicted in FIGS. 1 and 2, such a sensor arrangement may comprise one or more photosensors 72 supported by a bracket 74 adjacent the test surface 26 to direct an electronic beam at a test tape adhered to the surface 26 to detect movement of the tape, e.g., lifting or other separation from the test surface 26.

In an embodiment of the apparatus 20 such as depicted in the drawings, wherein a corrugated test surface such as the test surface 26 may be utilized, it may be advantageous to provide multiple photosensors 72 at spacings corresponding to the corrugations in the test surface 26 so as to detect sequential failures in the adhesion of the tape as may occur under a continual load. Alternatively, in other embodiments, it is contemplated that a single photosensor 72 may be utilized. In the illustrated embodiment, the bracket 74 is in the form of an elongated angled plate mounted to the table surface 25 adjacent the test surface 26. A portion of the bracket 74 is elevated above the test surface 26 and elongated mounting slots 76 in the bracket 74 provide for lateral movement of the bracket 74 toward and away from the test surface 26 to position the bracket 74 laterally away from the test surface 26 for placement thereon and removal therefrom of a tape and alternatively to position the bracket 74 and its photosensors 72 directly above a tape on the surface 26.

Figure 4:
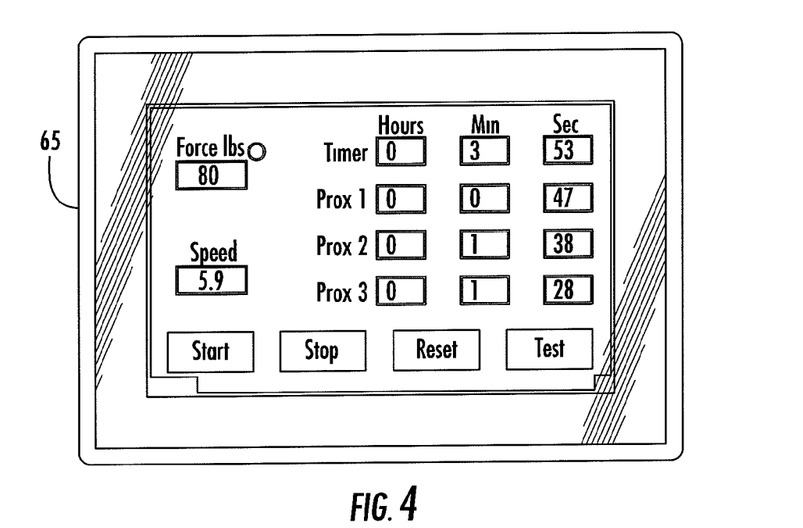
FIG. 4 is an elevational view of the operational control panel for the testing apparatus of the present invention.

The operation of the testing apparatus 20 may thus be understood with additional reference to FIGS. 5-9. Initially, the testing apparatus 20 is energized by supplying electrical power to the control box 45 and the air compressor 50, which charges the accumulator 52 and pressurizes each airflow circuit 54, 56. A length of an adhesive tape 78 is selected for testing and, based upon and according to the type and physical characteristics of the selected tape, a decision is made as to the pound force that should be applied for testing. The selected force is then input via the control panel 65 (FIG. 4) and, in turn, the programmable controller 66 energizes the appropriate actuating valve 62 or 64 for the linear actuator 44 or 46 appropriate for the selective force, while all of the associated exhaust valves 58A-58F or 60A-60F remain closed. The actuating valve 62 or 64 delivers pressurized air to the associated linear actuator 44, 46 to move its internal piston and the attached drive bracket 44A or 46A to a starting position at the end of the linear actuator most closely proximal the test surface 26. The cable tether 68 is then attached to the drive bracket 44A or 46A of the activated linear actuator 44, 46. The test apparatus 20 is thereby readied for operation.

Figure 5:
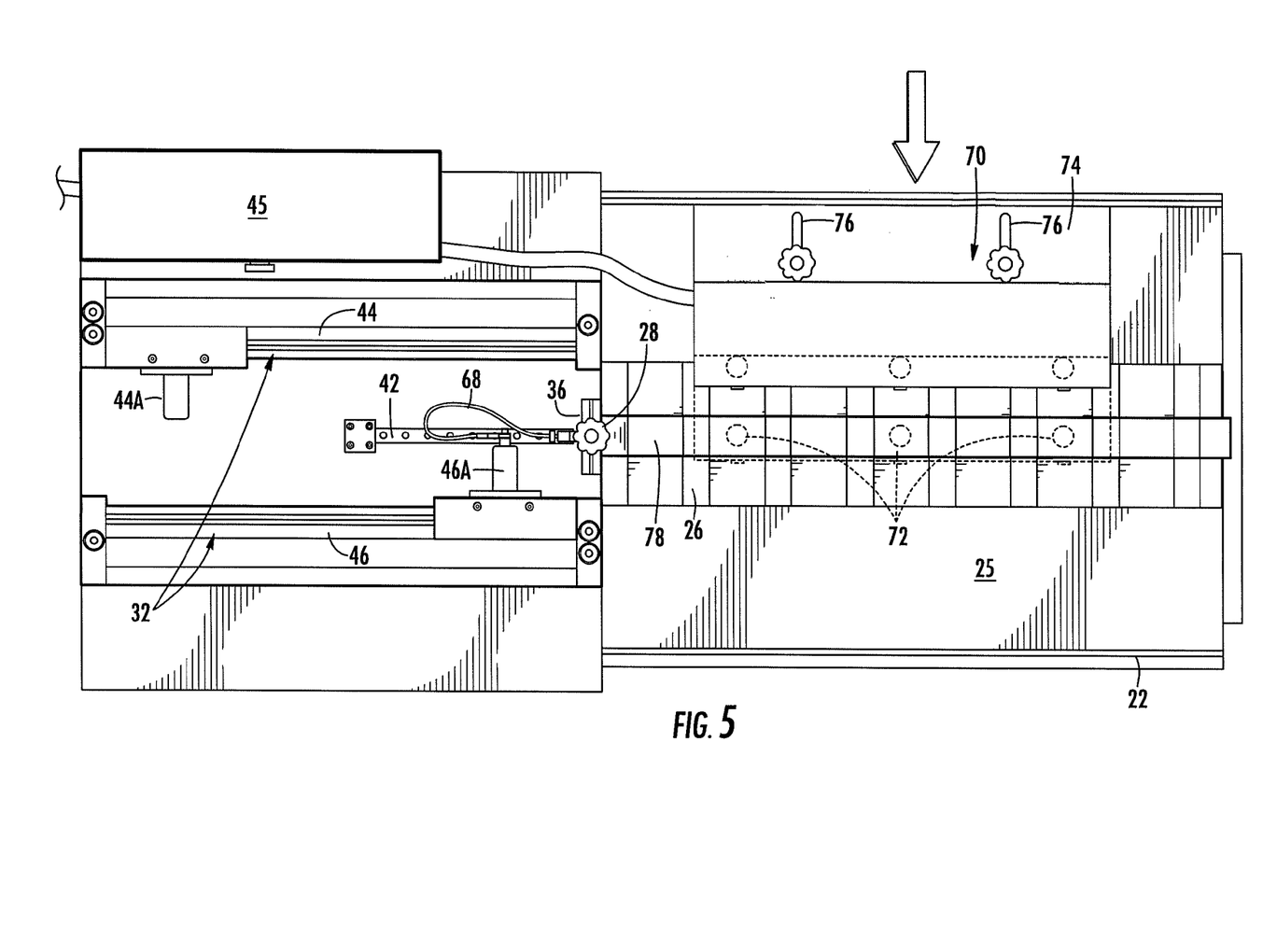
FIGS. 5-9 are top plan views of the testing apparatus similar to FIG. 2, depicting a typical sequence of operation of the apparatus.
Figure 6:
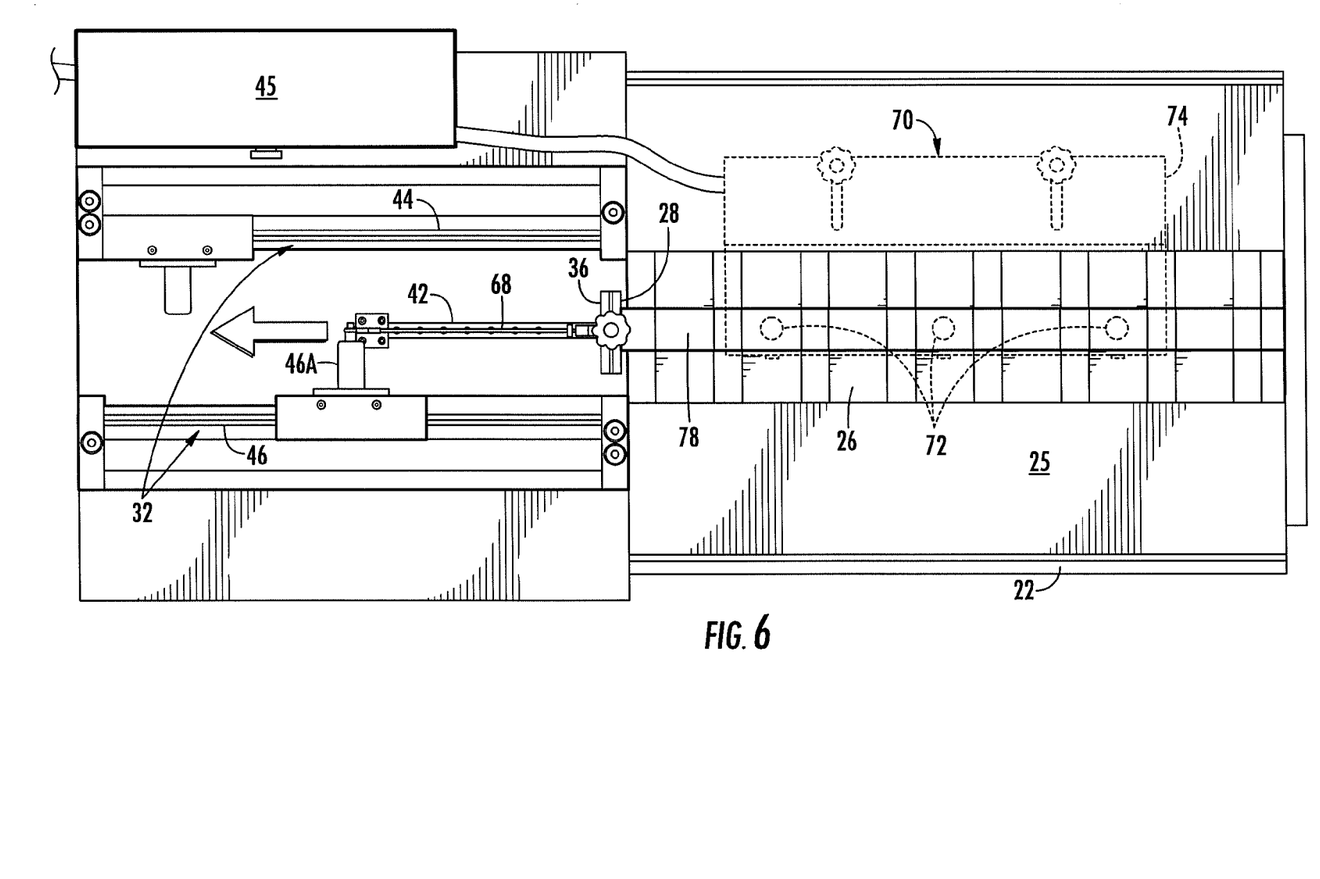

As representatively depicted in FIG. 5, the selected length of adhesive tape 78 to be tested is applied and securely adhered to the test surface 26 lengthwise therealong substantially in linear alignment with the guide rail 42, but with the end of the tape 78 most closely proximal the clamping device 28 left free and unadhered to the surface 26. The free end of the tape 78 is then placed within and securely grasped by tightening of the jaws 36 of the clamping device 28. With the tape 78 thusly prepared for testing, the test is initiated at the control panel 65, e.g., by pressing the "Test" button. Immediately thereupon, the appropriate exhaust valve 58A-58F or 60A-60F for the previously input pound force is opened, thereby opening a pathway for exhaust of pressurized air within the activated linear actuator 44 or 46. The piston of the linear actuator 44 or 46 and the associated drive bracket 44A or 46A is immediately driven toward the opposite end of the actuator 44 or 46 distal to the test surface 26.

As the piston and the drive bracket 44A or 46A accelerate, no force is initially applied to the tape 78 until the piston and the drive bracket 44A or 46A have advanced an initial length of travel sufficient to take up the slack in the cable tether 68 (FIG. 6) but immediately upon tautening of the cable tether 68, an abrupt impact force is exerted linearly along the free end of the tape 78. In the representative embodiment as illustrated wherein a corrugated test surface 26 simulates a cargo container, the amount of intended slack in the cable tether 68 is selected to ensure that, before the impact force is applied to the test tape 78, the drive bracket 44A or 46A of the active linear actuator 44 or 46 has reached a predetermined speed representative of impacts occurring in actual cargo handling usage. According to current cargo industry standards, securement systems must be capable of withstanding a 6 mph impact. However, as previously indicated, any other initial impact speed, or no impact speed at all, may be accomplished by adjustment of slack in the tether 68, or the provision of an alternative means of connecting the drive brackets 44A or 46A of the linear actuators 44, 46 to the clamping device, or by other modifications or adjustments in the airflow circuits, such as provision of different or additional valving arrangements, any or all of which are contemplated and intended to be within the scope and concept of the present invention.

Figure 7:
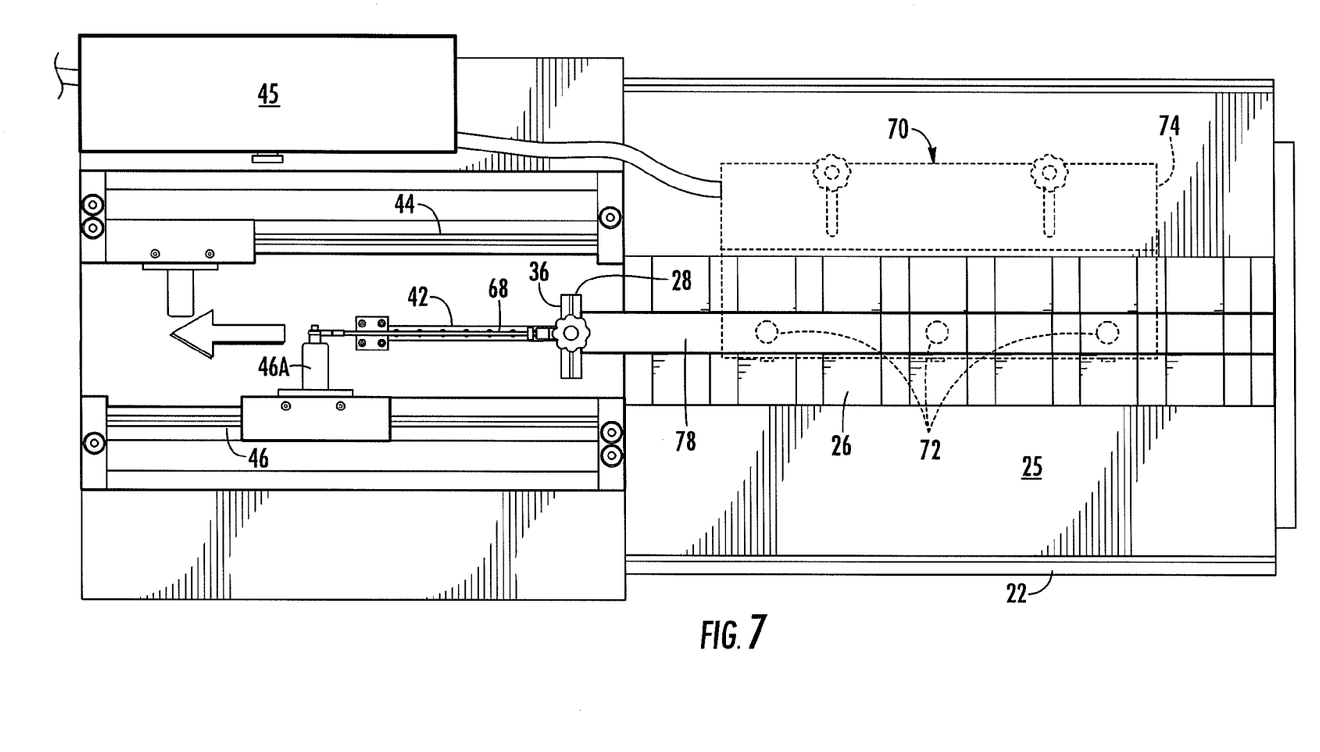
Figure 8:
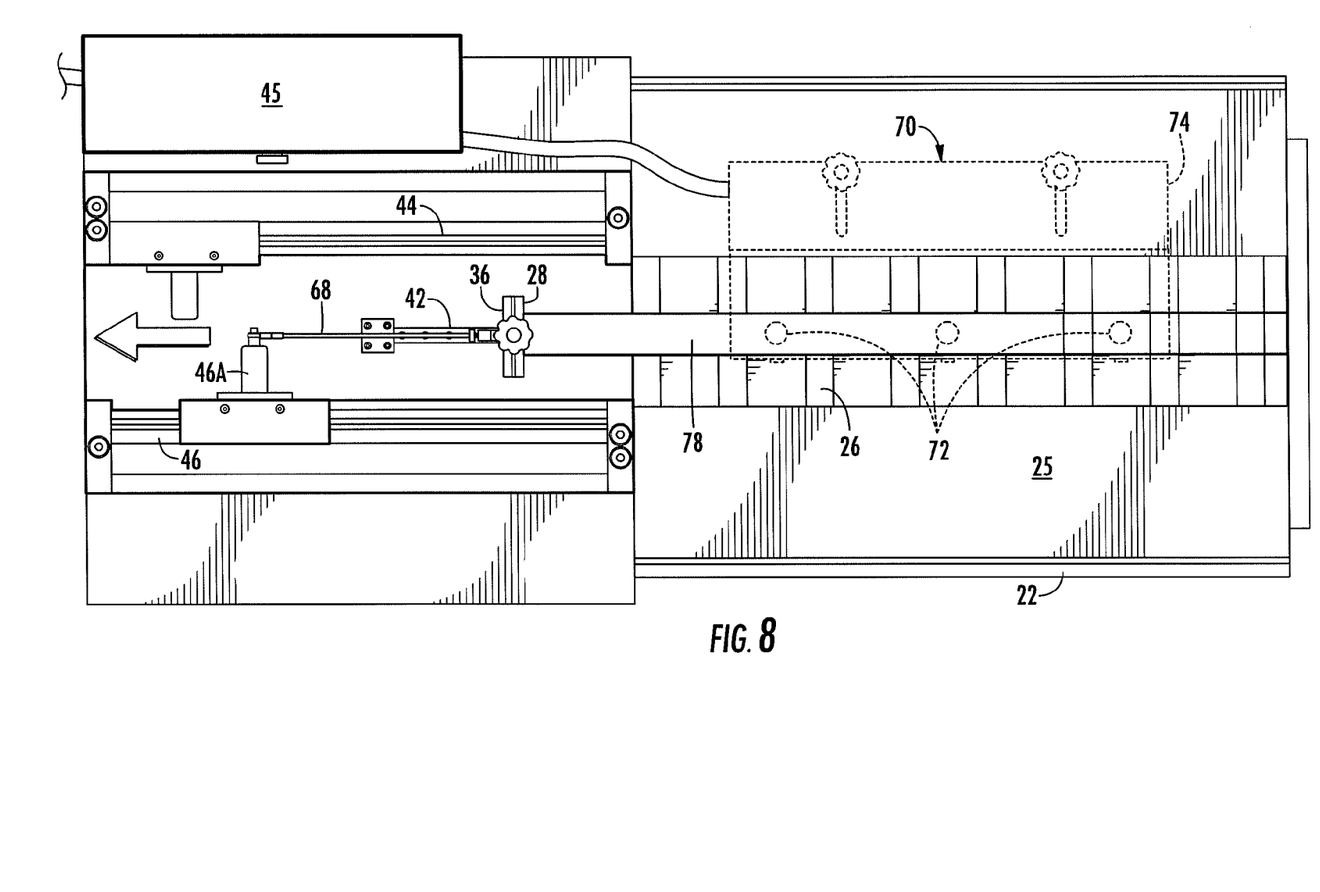
Figure 9:
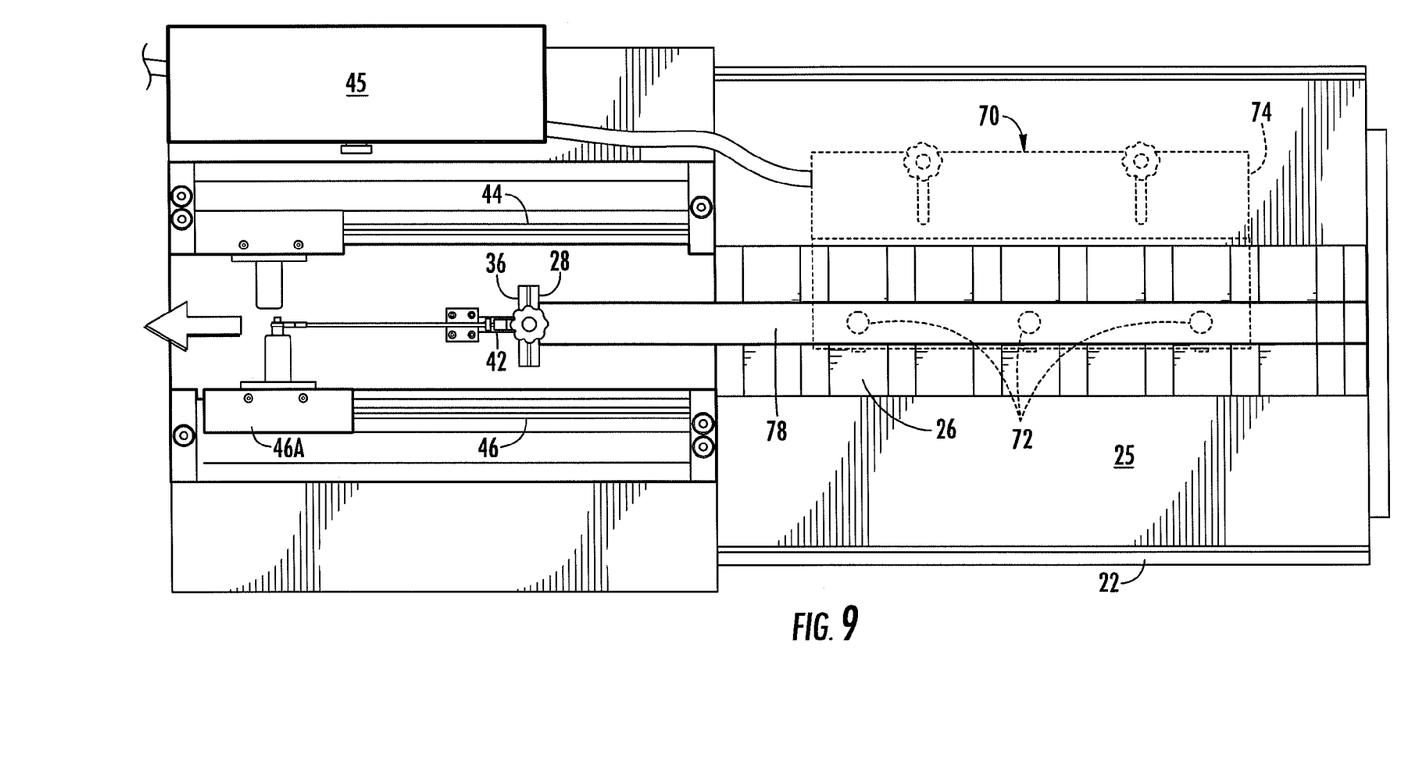

Depending upon the amount of the selected force in relation to the structure and composition of the tape 78, a failure may immediately occur in the tape 78, e.g., overcoming the adhesive bond of the tape 78 to the first corrugation linearly along the test surface 26 or even tearing the tape 78. In such case, the first photosensor 72 will recognize movement in the tape 78 as it separates from the test surface 26 at the first corrugation and will transmit an associated signal to the programmable controller 66 which records the elapsed time from the initiation of the test to the detected failure. However, in the intended manner of operation, the applied force is selected to be of an amount that the tape 78 is capable of at least initially resisting, whereby a failure in the tape 78 does not immediately occur. The air compressor 50 together with the accumulator 52 continue to maintain pressure within the associated airflow circuit 54, 56, such that the selected force is maintained and continues to be applied to the tape 78. After some period of time, the continued application of force to the tape 78 will cause separation of the tape 78 from the first corrugation in the test surface 26, which will be recognized by the first photosensor 72 and recorded by the programmable controller 66, as above described. This condition is represented in FIG. 7. As force continues to be applied to the tape 78, subsequent separations of the tape from the second and third corrugations in the test surface 26 will occur in sequence and similarly be detected by the second and third photosensors 72 and signalled to and recorded by the programmable controller 66 in the same manner, as represented respectively in FIGS. 8 and 9. At the conclusion of the test procedure, the control panel 65 will present the test results according to the total elapsed time of the test and the incremental elapsed times to first, second and third failures.

As will be understood, the arrangement of structural components in the test apparatus 20 as above-described serves to impose the force of the linear actuator 44 or 46 in direct linear alignment with the test tape 78, whereby the exerted force is applied entirely as a shear force to the tape. In actual use of any tape, e.g., especially cargo restraint tapes, forces applied to the tape will not necessarily be applied as a 100% shear force but may naturally be applied as a combination of shear and peel forces. To enable the test apparatus 20 to evaluate tape adhesion under such conditions, the apparatus may be equipped with an arrangement for selective inclination of the table surface 25, and in turn the test surface 26 thereon, such that the above-described test procedure imposes a combined shear and peel force on a test tape.

Figure 10:
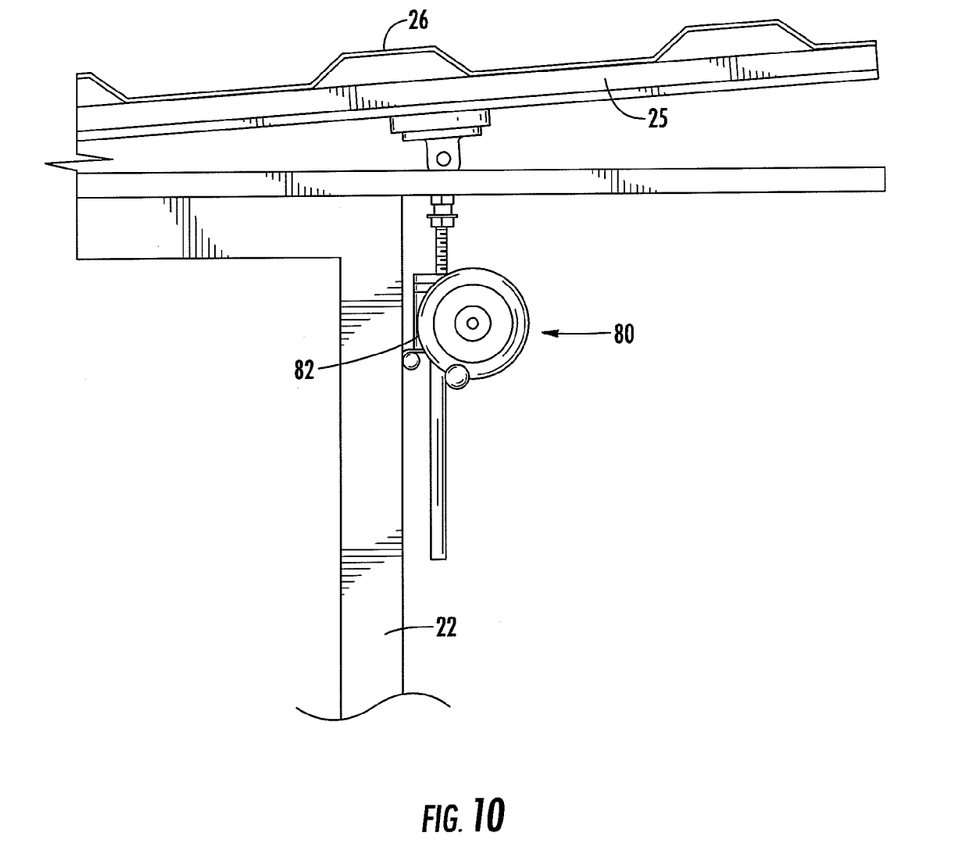
FIG. 10 is an elevational view of the inclination adjustment arrangement of the apparatus of the present invention.

Any of various mechanical arrangements may be utilized to accomplish inclination of the table surface 25 in selected increments. By way of example but without limitation, a representative mechanical adjusting arrangement is shown at 80 in FIG. 10. In this representative embodiment, the table surface 25 is hinged to the frame 22 at the end thereof adjacent the clamping device 28 and the actuator arrangement 32, with the opposite end of the table surface 25 affixed to the adjusting arrangement 80, which may for example be in the form of a screw jack mechanism 82. Advantageously, the screw jack mechanism 82 allows infinitely fine angular adjustments in the inclination of the table surface 25 within the overall limits of the extensibility of the mechanism 82.

In addition, it will be understood that it may be advantageous to test tapes under different environmental or ambient conditions. For example, cargo containers may not be provided with any ventilation arrangement, whereby extreme swings in temperature and humidity may occur within the confines of a container depending upon various factors such as the manner of shipment and routes taken during shipment. Advantageously, the test apparatus 20 of the present invention is a self-contained structure which, via the cart-mounted frame, may be transported from one location to another and, for example, moved between differing ambient environments for testing under different ambient conditions. When testing under extreme conditions of elevated or extremely low temperatures and/or humidity, or under even more hazardous conditions, it may be undesirable or impossible for an operator to be subjected to the same conditions. Accordingly, the programmable controller 66 of the apparatus 22 is equipped for remote input and actuation via any suitable remote controller, which may be connected to the apparatus by a wired or wireless connection, representatively indicated only schematically at 84 in FIG. 3.

It will therefore be recognized and understood that the present test apparatus 20 provides numerous improvements and advantages over rudimentary test procedures employed heretofore. Most fundamentally, the apparatus 20 of the present invention enables testing of adhesive tapes to be precisely fine-tuned to simulate any of various conditions and parameters a tape may undergo in normal operation and to precisely replicate any such test protocol reliably and repeatedly. The apparatus is further adapted for testing any of various types of tapes on any of various types of test surfaces.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. Apparatus for testing adhesion of an adhesive tape to a bonding surface under a load applied to the tape, the apparatus comprising:
(a) a test surface to which is adhered a length of adhesive tape to be tested,
(b) a clamping device for grasping a free edge of the adhesive tape to be tested,
(c) a guide for constraining the clamping device to move in a defined linear direction relative to the test surface, and
(d) an actuator arrangement for driving the clamping device along the guide at a selected speed and with a selected force to apply the force to the tape adhered to the test surface, the actuator arrangement including:
  (i) a first linear actuator arrangement operable to generate the selected force within a first range of force values,
  (ii) a second linear actuator arrangement operable to generate the selected force within a second range of force values,
  (iii) a motor for driving the linear actuators arrangements, and
  (iv) a first selector arrangement for selectively connecting the motor alternately to the first and second actuator arrangements according to the selected force to be applied to the clamping device.

2. Apparatus for testing adhesion of an adhesive tape to a bonding surface under a load applied to the tape according to claim 1, wherein the motor comprises an air compressor.

3. Apparatus for testing adhesion of an adhesive tape to a bonding surface under a load applied to the tape according to claim 2, wherein the motor further comprises an accumulator communicated with the air compressor to receive and store pressurized air.

4. Apparatus for testing adhesion of an adhesive tape to a bonding surface under a load applied to the tape according to claim 2, wherein the first linear actuator arrangement comprises a first linear actuator, a first plurality of valves associated with the first linear actuator, each valve of the first plurality of valves being operable for passage of pressurized air therethrough at a respective predetermined rate different from each other valve of the first plurality of valves.

5. Apparatus for testing adhesion of an adhesive tape to a bonding surface under a load applied to the tape according to claim 4, wherein the second linear actuator arrangement comprises a second linear actuator, a second plurality of valves associated with the second linear actuator, each valve of the second plurality of valves being operable for passage of pressurized air therethrough at a respective predetermined rate different from each other valve of the second plurality of valves.

6. Apparatus for testing adhesion of an adhesive tape to a bonding surface under a load applied to the tape according to claim 4, wherein the selector arrangement selectively actuates any selected one of the first or second plurality of valves.

7. Apparatus for testing adhesion of an adhesive tape to a bonding surface under a load applied to the tape according to claim 6, wherein the actuator arrangement includes a tether attached to the clamping device and selectively attachable alternately to the first and second linear actuators.

8. Apparatus for testing adhesion of an adhesive tape to a bonding surface under a load applied to the tape according to claim 7, wherein the tether is of a selected length between the clamping device and a starting position of each of the first and second linear actuators to be initially slackened upon actuation thereof for acceleration of the selected first or second linear actuator to a selected speed before tautening of the tether to apply the selected force on the tape to be tested as an initial impact force and thereafter to maintain application of the selected force continuously on the tape to be tested.

9. Apparatus for testing adhesion of an adhesive tape to a bonding surface under a load applied to the tape according to claim 1, wherein the actuator arrangement includes a tether attached to the clamping device and selectively attachable alternately to the first and second linear actuator arrangements.

10. Apparatus for testing adhesion of an adhesive tape to a bonding surface under a load applied to the tape according to claim 1, further comprising a sensor arrangement for detecting release of the tape from the test surface under the force applied by the actuator arrangement.

11. Apparatus for testing adhesion of an adhesive tape to a bonding surface under a load applied to the tape according to claim 10, wherein the sensor arrangement comprises a plurality of photosensors directed at spacings along the test surface.

12. Apparatus for testing adhesion of an adhesive tape to a bonding surface under a load applied to the tape according to claim 1, further comprising a frame to which the test surface, the clamping device, the guide, and the actuator arrangement are commonly mounted.

13. Apparatus for testing adhesion of an adhesive tape to a bonding surface under a load applied to the tape according to claim 12, wherein the frame comprises a wheeled cart.

14. Apparatus for testing adhesion of an adhesive tape to a bonding surface under a load applied to the tape according to claim 1, further comprising a control arrangement for remote actuation of the actuator arrangement.

15. Apparatus for testing adhesion of an adhesive tape to a bonding surface under a load applied to the tape according to claim 1, wherein the test surface is selectively attachable and detachable for interchange of multiple alternative test surfaces.

16. Apparatus for testing adhesion of an adhesive tape to a bonding surface under a load applied to the tape according to claim 1, further comprising a table surface to which the test surface is mounted and an adjusting arrangement for selectively setting the table in a horizontal disposition or a disposition inclined relative to horizontal, for selectively varying the direction of application of the selected force on the tape to be tested.

17. Apparatus for testing adhesion of an adhesive tape to a bonding surface under a load applied to the tape according to claim 1, wherein the test surface is selectively attachable and detachable for interchange of multiple alternative test surfaces.

18. Apparatus for testing adhesion of an adhesive tape to a bonding surface under a load applied to the tape, the apparatus comprising:
 (a) a test surface to which is adhered a length of adhesive tape to be tested,
 (b) a clamping device for grasping a free edge of the adhesive tape to be tested,
 (c) a guide for constraining the clamping device to move in a defined linear direction relative to the test surface, and
 (d) an actuator arrangement for driving the clamping device along the guide at a selected speed and with a selected force to apply the force to the tape adhered to the test surface, the actuator arrangement including:
   (i) at least one linear actuator arrangement operable to generate the selected force within a range of force values, and
   (ii) a motor for driving the linear actuator arrangement, wherein the motor comprises an air compressor and an accumulator communicated with the air compressor to receive and store pressurized air.

19. Apparatus for testing adhesion of an adhesive tape to a bonding surface under a load applied to the tape, the apparatus comprising:
 (a) a test surface to which is adhered a length of adhesive tape to be tested,
 (b) a clamping device for grasping a free edge of the adhesive tape to be tested,
 (c) a guide for constraining the clamping device to move in a defined linear direction relative to the test surface, and
 (d) an actuator arrangement for driving the clamping device along the guide at a selected speed and with a selected force to apply the force to the tape adhered to the test surface, the actuator arrangement including:
   (i) at least one linear actuator arrangement operable to generate the selected force within a range of force values, and
   (ii) a motor for driving the linear actuator arrangement, wherein the linear actuator arrangement comprises a linear actuator, a plurality of valves associated with the first linear actuator, each valve being operable for passage of pressurized air therethrough at a respective predetermined rate different from each other valve.

20. Apparatus for testing adhesion of an adhesive tape to a bonding surface under a load applied to the tape according to claim 18 or 19, wherein the actuator arrangement further comprises a selector arrangement for selectively actuating any selected one of the plurality of valves.

21. Apparatus for testing adhesion of an adhesive tape to a bonding surface under a load applied to the tape according to claim 18 or 19, wherein the actuator arrangement includes a tether attached to the clamping device and to the linear actuator.

22. Apparatus for testing adhesion of an adhesive tape to a bonding surface under a load applied to the tape according to claim 21, wherein the tether is of a selected length between the clamping device and a starting position of the linear actuator to be initially slackened upon actuation thereof for acceleration of the linear actuator to a selected speed before tautening of the tether to apply the selected force on the tape to be tested as an initial impact force and thereafter to maintain application of the selected force continuously on the tape to be tested.

23. Apparatus for testing adhesion of an adhesive tape to a bonding surface under a load applied to the tape according to claim 18 or 19, further comprising a sensor arrangement for detecting release of the tape from the test surface under the force applied by the actuator arrangement.

24. Apparatus for testing adhesion of an adhesive tape to a bonding surface under a load applied to the tape according to claim 23, wherein the sensor arrangement comprises a plurality of photosensors directed at spacings along the test surface.

25. Apparatus for testing adhesion of an adhesive tape to a bonding surface under a load applied to the tape according to claim 18 or 19, further comprising a frame to which the test surface, the clamping device, the guide, and the actuator arrangement are commonly mounted.

26. Apparatus for testing adhesion of an adhesive tape to a bonding surface under a load applied to the tape according to claim 25, wherein the frame comprises a wheeled cart.

27. Apparatus for testing adhesion of an adhesive tape to a bonding surface under a load applied to the tape according to claim 18 or 19, further comprising a control arrangement for remote actuation of the actuator arrangement.

28. Apparatus for testing adhesion of an adhesive tape to a bonding surface under a load applied to the tape according to claim 18 or 19, further comprising a table surface to which the test surface is mounted and an adjusting arrangement for selectively setting the table in a horizontal disposition or a disposition inclined relative to horizontal, for selectively varying the direction of application of the selected force on the tape to be tested.

* * * * *